United States Patent [19]

Fukuda et al.

[11] Patent Number: 4,808,293
[45] Date of Patent: Feb. 28, 1989

[54] OXYGEN SENSOR AND METHOD OF MAKING SUCH SENSOR

[75] Inventors: Hiroshi Fukuda; Takeshi Nagai, both of Nara; Kenzo Ohji, Ikoma, all of Japan

[73] Assignee: Matsushita Electric Industrial Co., Ltd., Japan

[21] Appl. No.: 135,093

[22] Filed: Dec. 18, 1987

[30] Foreign Application Priority Data

Dec. 19, 1986 [JP] Japan .................. 61-304115
Dec. 19, 1986 [JP] Japan .................. 61-304130
Apr. 23, 1987 [JP] Japan .................. 62-100386
Apr. 23, 1987 [JP] Japan .................. 62-100388

[51] Int. Cl.⁴ ............................................. G01N 27/58
[52] U.S. Cl. .................................. 204/410; 427/126.5
[58] Field of Search ................ 204/410, 425, 426, 15; 427/126.5

[56] References Cited

U.S. PATENT DOCUMENTS

| 3,411,073 | 11/1968 | Marr | 324/33 |
|---|---|---|---|
| 3,691,023 | 9/1972 | Ruka et al. | 204/1 T |
| 3,787,308 | 1/1974 | Malaspina et al. | 204/11 T X |
| 3,820,015 | 6/1974 | Jeunehomme | 73/23 X |
| 4,158,166 | 6/1979 | Isenberg | 204/1 T X |
| 4,272,331 | 6/1981 | Hetrick | 204/1 T |
| 4,505,806 | 3/1985 | Yamada | 204/425 |
| 4,728,411 | 3/1988 | Mase et al. | 204/425 |

FOREIGN PATENT DOCUMENTS

| 59-26895 | 7/1984 | Japan . | |
| 186750 | 9/1985 | Japan | 204/425 |

OTHER PUBLICATIONS

Nippon Electrical Glass, Ref. No. 8509-02, Oct., 1985.
Iwaki Glass, Nov. 1984.

Primary Examiner—G. L. Kaplan
Attorney, Agent, or Firm—Lowe, Price, LeBlanc, Becker & Shur

[57] ABSTRACT

An oxygen conductive solid electrolyte plate has first and second opposite surfaces, First and second electrodes fixedly extend on the first and second surfaces of the electrolyte plate respectively. A spacing frame hermetically secured to the first surface of the electrolyte plate surrounds the first electrode. The spacing frame has an opening. A sealing plate hermetically secured to the spacing frame defines a chamber in conjunction with the electrolyte plate and the spacing frame. The chamber accommodates the first electrode and opens into an environment only via a window defined by the opening in the spacing frame. The window allows oxygen molecules to flow from the environment into the chamber by diffusion.

20 Claims, 2 Drawing Sheets

OXYGEN SENSOR AND METHOD OF MAKING SUCH SENSOR

BACKGROUND OF THE INVENTION

1. Field of the Invention

This invention relates to an oxygen sensor and also relates to a method of manufacturing the same.

2. Description of the Prior Art

U.S. Pat. No. 4,158,166 discloses a combustibles sensor probe including a closed end tubular housing member having a gas diffusion limiting aperture in the closed end. The sensor probe also includes a solid electrolyte electrochemical cell sealed within the tubular housing to define an internal chamber and an air or oxygen chamber. The solid electrolyte electrochemical cell consists of an oxygen ion conductive solid electrolyte member, and electrodes disposed on opposite surfaces thereof. The sensor probe can be used to measure both oxygen and combustibles.

Japanese published examined patent application 59-26895 discloses a similar sensor probe.

SUMMARY OF THE INVENTION

It is an object of this invention to provide an oxygen sensor which can operate in a wide range of temperatures.

It is another object of this invention to provide an easy method of manufacturing an oxygen sensor.

In an oxygen sensor of this invention, an oxygen ion conductive solid electrolyte plate has first and second opposite surfaces. First and second electrodes fixedly extend on the first and second surfaces of the electrolyte plate respectively. A spacing frame hermetically secured to the first surface of the electrolyte plate surrounds the first electrode. The spacing frame has an opening. A sealing plate hermetically secured to the spacing frame defines a chamber in conjunction with the electrolyte plate and the spacing frame. The chamber accommodates the first electrode and opens into an environment only via a window defined by the opening in the spacing frame. The window allows oxygen molecules to flow from the environment into the chamber by diffusion.

In a method of manufacturing an oxygen sensor according to this invention, an electrode is formed on a surface of an oxygen ion conductive solid electrolyte plate. After the electrode is formed on the surface of the electrolyte plate, a predetermined pattern of glass paste is printed on the surface of the electrolyte plate. The predetermined pattern of the glass paste surrounds the electrode. The glass paste includes organic binder and fine glass particles. A sealing plate is placed on the printed pattern of the glass paste. An assembly of the electrolyte plate, the pattern of the glass paste, and the sealing plate is fired. Accordingly, the pattern of the glass paste is converted to a corresponding pattern of fired glass film, and the electrolyte plate and the sealing plate are hermetically secured to the pattern of the fired glass film. The electrolyte plate, the sealing plate, and the pattern of the fired glass film define a chamber accommodating the electrode.

In another method of manufacturing an oxygen sensor according to this invention, an electrode is formed on a surface of an oxygen ion conductive solid electrolyte plate. After the electrode is formed on the surface of the electrolyte plate, a predetermined pattern of Ti foil sandwiched between layers of an Ag-Cu alloy is placed on the surface of the electrolyte plate. The predetermined pattern of the Ti foil surrounds the electrode. A sealing plate is placed on the pattern of the Ti foil. An assembly of the electrolyte plate, the pattern of the Ti foil, and the sealing plate is fired so that the electrolyte plate and the sealing plate are hermetically secured to the pattern of the Ti foil. The electrolyte plate, the sealing plate, and the pattern of the Ti foil define a chamber accommodating the electrode.

BRIEF DESCRIPTION OF THE DRAWINGS

Like and corresponding elements are denoted by the same reference characters throughout the drawings.

DESCRIPTION OF THE FIRST PREFERRED EMBODIMENT

Figure 1:
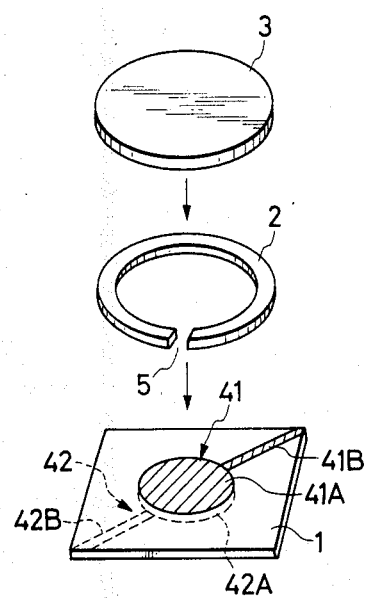
FIG. 1 is an exploded perspective view of an oxygen sensor according to a first embodiment of this invention.
Figure 2:
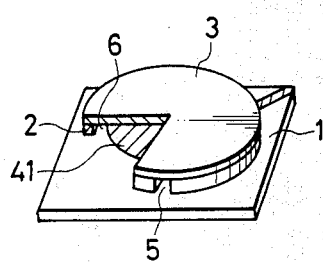
FIG. 2 is a perspective, partially cutaway view of the oxygen sensor of FIG. 1.

With reference to FIGS. 1 and 2, an oxygen sensor according to a first embodiment of this invention includes an oxygen ion conductive solid electrolyte plate 1, a spacing frame or spacer 2, and a sealing plate or cover 3.

The electrolyte plate 1 is square. Two electrodes 41 and 42 are fixedly formed on opposite surfaces of the electrolyte plate 1 respectively. It should be noted that the electrode 42 is shown by the broken phantom lines in FIG. 1. The electrode 41 has a circular main portion 41A and a line portion 41B. The main portion 41A of the electrode 41 extends over a central portion of the upper surface of the electrolyte plate 1. The line portion 41B of the electrode 41 extends between the main portion 41A of the electrode 41 and a corner of the electrolyte plate 1. Similarly, the electrode 42 has a circular main portion 42A and a line portion 42B. The main portion 42A of the electrode 42 extends over a central portion of the lower surface of the electrolyte plate 1 and in alignment with the main portion 41A of the other electrode 41. The line portion 42B of the electrode 42 extends between the main portion 42A of the electrode 42 and a corner of the electrolyte plate 1 opposite the corner at which the line portion 41B of the other electrode 41 terminates.

The spacing frame 2 is in the form of a ring having an opening 5. The inside diameter of the spacing frame 2 is slightly greater than the outside diameter of the main portion 41A of the electrode 41. The spacing frame 2 is hermetically attached to the upper surface of the electrolyte plate 1. The spacing frame 2 extends coaxially with the main portion 41A of the electrode 41 and surrounds the latter.

The sealing plate 3 consists of a disk having a diameter essentially equal to the outside diameter of the spacing frame 2. The sealing plate 3 is hermetically attached to the upper surface of the spacing frame 2. Accordingly, the spacing frame 2 extends between the electrolyte plate 1 and the sealing plate 3. The sealing plate 3 extends coaxially with the spacing frame 2. The sealing plate 3, the spacing frame 2, and the electrolyte plate 1 define a chamber 6 which opens into an environment via only a window defined by the opening 5 of the spacing frame 2. The main portion 41A of the electrode 41 resides in the chamber 6. The thickness of the spacing frame 2 determines a dimension or height of the window 5.

The electrodes 41 and 42 can be connected to a DC power source (not shown) via the line portions 41B and 42B, and external leads (not shown). When a DC electric field is applied between the two electrodes 41 and 42 in such a way that the electrodes 41 and 42 form a cathode and an anode respectively, the oxygen molecules in the chamber 6 are ionized at the cathode electrode 41 and are then transported from the cathode electrode 41 to the anode electrode 42 via the electrolyte plate 1. At the anode electrode 42, the transported oxygen ions react on each other and form oxygen molecules. The oxygen molecules are emitted from the anode electrode 42 to the environment. At the same time, oxygen molecules flow from the environment into the chamber 6 through the window 5 by diffusion. The rate of flow of diffusing oxygen molecules from the environment into the chamber 6 is limited to a given value depending on a diffusion flow resistance by the window 5. These processes result in a limited ionic current flowing between the electrodes 41 and 42. The limited ionic current flowing between the electrodes 41 and 42 increases linearly with the oxygen concentration in the environment (see FIG. 6). In general, as the size of the window 5 decreases and thus the diffusion flow resistance by the window 5 increases, the oxygen sensor can operate at a lower temperature.

Generally, in cases where the window 5 can be regarded as being circular and the oxygen sensor is required to operate at a temperature of 400° C., the window 5 is preferably about 30 micrometers in diameter and 1 millimeter in length. In cases where the oxygen sensor is required to operate at temperatures below 400° C., the window 5 is preferably smaller.

In general, the electrodes 41 and 42 are formed on the electrolyte plate 1 before the spacing frame 2 is provided on the electrolyte plate 1. The spacing frame 2 consists of a thin member such as a plated film, a fired film, a vacuum deposited film, a sputtered film, or a thin foil. The window or opening 5 of desired small dimensions is formed by an etching technique or a masking technique in connection with the formation of the spacing frame 2 on the electrolyte plate 1. For example, the etching technique allows the window 5 to be of a submicron pattern. In cases where the flatness of the electrolyte plate 1 is required to be less than some micrometers, the electrolyte plate 1 is finely polished before the formation of the spacing frame 2 on the electrolyte plate 1. In some of other cases, it is unnecessary to polish the electrolyte plate 1. Generally, the masking technique is fit to form a larger window 5 such as a window of dimensions in 100-micrometer order.

DESCRIPTION OF THE SECOND PREFERRED EMBODIMENT

Figure 3:
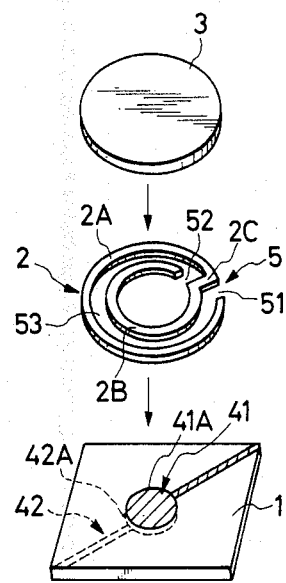
FIG. 3 is an exploded perspective view of an oxygen sensor according to a second embodiment of this invention.

FIG. 3 shows a second embodiment of this invention which is similar to the embodiment of FIGS. 1 and 2 except for design changes indicated hereinafter.

In the embodiment of FIG. 3, a spacing frame 2 has concentric rings 2A and 2B connected by a radial bridge 2C. The inside diameter of the inner ring 2B is slightly greater than the diameter of the main portion 41A of the electrode 41. The outside diameter of the outer ring 2A is essentially equal to the diameter of the sealing plate 3. The sealing plate 3 is hermetically attached to the upper surface of the spacing frame 2. The inner ring 2B, the sealing plate 3, and the electrolyte plate 1 define the chamber 6 (see FIG. 2) accommodating the main portion 41A of the electrode 41.

The rings 2A and 2B have openings 51 and 52 respectively. The rings 2A and 2B are spaced radially so that an annular space 53 extends between the rings 2A and 2B. One end of the annular space 53 communicates with the chamber 6 (see FIG. 2) via the opening 52 of the inner ring 2B. The other end of the annular space 53 communicates with the environment via the opening 51 of the outer ring 2A. The openings 51 and 52, and the annular space 53 constitute the window 5 connecting the chamber 6 (see FIG. 2) and the environment. The window 5 has a spiral path. The spiral structure of the window 5 increases the diffusion flow resistance, enabling the oxygen sensor to operate at a lower temperature.

In cases where the main portions 41A and 42A of the electrodes 41 and 42 are 6 millimeters in diameter and where the window 5 is 50 micrometers in height, 400 micrometers in width, and 25 millimeters in length, the limited ionic current is about 100 microamperes for the environment oxygen concentration equal to 21% when the operating temperature of the oxygen sensor is 400° C. In cases where the window 5 is 20 micrometers in height, 200 micrometers in width, and 12 millimeters in length, the oxygen sensor can operate at a temperature of 350° C.

The spacing frame 2 is preferably composed of a fired glass film. The spacing frame 2 may be composed of other films or foils such as used in the embodiment of FIGS. 1 and 2. It is also preferable that the spacing frame 2 is composed of a Ti foil sandwiched between and coated with layers made of Ag-Cu alloy.

In cases where the spacing frame 2 is composed of the fired glass film, the oxygen sensor is fabricated or manufactured as follows. The electrodes 41 and 42 are preformed on opposite surfaces of the electrolyte plate 1. Glass paste containing organic binder and fine glass particles is printed in a desired pattern on the surface of the electrolyte plate 1 on which the electrode 41 extends. Since the printed glass paste will form the spacing frame 2 as will be made clear hereinafter, the pattern of the glass paste is chosen to correspond to the shape of the spacing frame 2. The desired pattern of the glass paste is designed so as to surround the main portion 41A of the electrode 41. After the glass paste is printed, the sealing plate 3 is piled on the pattern of the glass paste. In this way, a provisional assembly including the electrolyte plate 1, the glass paste, and the sealing plate 3 is prepared. The assembly is fired in a furnace. As a result, the glass paste changes to a fired glass film forming the spacing frame 2. In addition, the electrolyte plate 1 and the sealing plate 3 are hermetically bonded to the fired glass film, that is, the spacing frame 2. The glass paste printing process allows an easy formation of the fired glass film having a thickness in the range of 10 to 100 micrometers. During the glass paste printing process, a masking technique is generally used to obtain the desired pattern of the printed glass paste having a spiral passage or space which will form the spiral window 5 with a width in the order of 100 micrometers.

In order to obtain the fired glass film of an essentially uniform thickness, it is preferable that the glass paste contains a mixture of glass material with a low melting temperature and small particles with a high melting temperature. When the previously-mentioned provisional assembly is fired in the furnace, the assembly is heated to a temperature near the melting point of the glass so that the glass film becomes soft. In cases where the glass paste has no particles with a high melting point, since the thickness of the glass film is determined by the gravity and the viscosity of the glass which sensitively depends on the temperature, a small change of the firing temperature causes a large variation in the thickness of the glass film. In cases where the glass paste contains a mixture of glass material with a low melting temperature and small particles with a high melting temperature, the thickness of the glass film is determined by the small particles because the particles do not become soft at a temperature near the melting point of the glass. The small particles are preferably made of $BaO-TiO_2-SiO_2$ ceramic because of its superior wettability to the glass and its excellent stability at a temperature higher than 1,000° C. The diameter of the small particles is preferably in the range of 10 to 50 micrometers, allowing easy printing of the glass paste. The glass material is preferably made of crystalline glass of $PbO-ZnO-B_2O_3$, allowing the glass paste to be fired at a temperature lower than 500° C. and also enabling the fired glass film to be stable at a temperature up to 450° C. The glass material may be made of other glasses such as containing PbO, $Na_2O$, $SiO_2$, BaO, $B_2O_3$, CaO, and ZnO.

In cases where the spacing frame 2 is composed of a Ti foil sandwiched between layers made of an Ag-Cu alloy, the oxygen sensor is fabricated or manufactured as follows. The electrodes 41 and 42 are preformed on opposite surfaces of the electrolyte plate 1. A Ti foil sandwiched between and coated with layers made of an Ag-Cu alloy is preformed in a given pattern on the surface of the electrolyte plate 1. Since the Ti foil will form the spacing frame 2, the pattern of the Ti foil is designed to correspond to the spiral shape of the spacing frame 2. The pattern of the Ti foil is also designed to surround the main portion 41A of the electrode 41. The sealing plate 3 is piled up on the pattern of the Ti foil. In this way, a provisional assembly including the electrolyte plate 1, the Ti foil, and the sealing plate 3 is prepared. The assembly is heated in a furnace supplied with an inert atmosphere or exposed to vacuum. As a result, the electrolyte plate 1 and the sealing plate 3 are hermetically bonded to the Ti foil forming the spacing frame 2. An etching technique allows easy formation of the Ti foil in a spiral pattern. For example, the spiral window 5 having a width in the order of 100 micrometers is easily formed by use of the etching technique. Since the Ti foil has a uniform thickness, the height of the window 5 can be accurately set to a given value. The layers or films sandwiching the Ti foil are preferably made of a eutectic Ag-Cu alloy, allowing the Ti foil to be bonded to the electrolyte plate 1 and the sealing plate 3 at a low temperature, that is, a eutectic temperature of about 780° C. The films sandwiching the Ti foil may be made of other Ag-Cu alloys.

The electrolyte plate 1 is preferably made of partially or fully stabilized $ZrO_2$ doped with Y, Ca, Sc, and Ba because of its stable ion conductivity. The electrolyte plate 1 may be of other types made of $ZrO_2$, $Bi_2O_3$, and $ErO_2$.

The sealing plate 3 is preferably made of material selected from a group of $ZrO_2$, glass, and forsterite. Since each of these materials has essentially the same thermal expansion coefficient as that of the electrolyte plate 1 made of stabilized $ZrO_2$, the oxygen sensor can operate stably even in cases where the oxygen sensor is subjected to many heat cycles between room temperature and operating temperature. It should be noted that the thermal expansion coefficient of electrolyte plate 1 made of stabilized $ZrO_2$ is about $100 \times 10^{-7}/°C$.

DESCRIPTION OF THE THIRD PREFERRED EMBODIMENT

Figure 4:
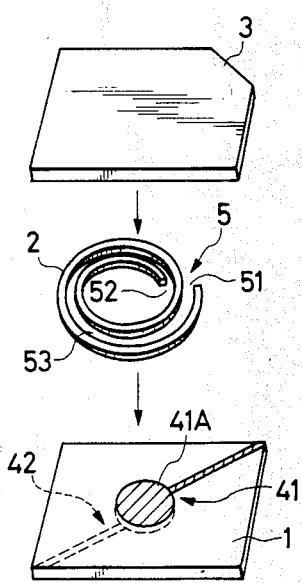
FIG. 4 is an exploded perspective view of an oxygen sensor according to a third embodiment of this invention.

FIG. 4 shows a third embodiment of this invention which is similar to the embodiment of FIG. 3 except for design changes indicated hereinafter.

In the embodiment of FIG. 4, a spacing frame 2 is spiral, having an outer opening 51, an inner opening 52, and a spiral path 53 connecting the openings 51 and 52. The outer opening 51 is exposed to the environment. The inner opening 52 is exposed to the chamber 6 (see FIG. 2) accommodating the main portion 41A of the electrode 41. The openings 51 and 52, and the spiral path 53 constitute a spiral window 5 connecting the chamber 6 (see FIG. 2) and the environment. A sealing plate 3 is larger than the spacing frame 2. The sealing plate 3 is in the form of a square with a cut corner. The sealing plate 3 has a portion projecting outwardly from the spacing frame 2 and covering or concealing the outer opening 51 as seen from above. Similarly, the electrolyte plate 1 has a portion projecting outwardly from the spacing frame 2 and covering or concealing the outer opening 51 as seen from below. The projecting portions of the sealing plate 3 and the electrolyte plate 2 are distant from each other by a gap corresponding to the thickness of the spacing frame 2. The projecting portions of the sealing plate 3 and the electrolyte plate 2 prevent dusts, having sizes larger than a thickness of the gap between these projecting portions, from moving to the outer opening 51 from the environment. Accordingly, the window 5 is prevented from clogging due to such dust contamination.

DESCRIPTION OF THE FOURTH PREFERRED EMBODIMENT

Figure 5:
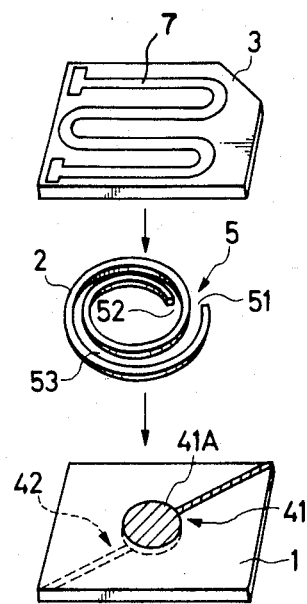
FIG. 5 is an exploded perspective view of an oxygen sensor according to a fourth embodiment of this invention.

FIG. 5 shows a fourth embodiment of this invention which is similar to the embodiment of FIG. 4 except for design changes indicated hereinafter.

In the embodiment of FIG. 5, a resistor or resistive film 7 forming a heater element is fired on the sealing plate 3. In cases where the oxygen sensor is provided with a thermally insulating package, when an electric power of about 2 W is applied to the resistive film 7, the oxygen sensor can be heated up to 400° C. The temperature coefficient of the resistance of the resistive film 7 is preferably positive and as high as possible, allowing self temperature control. The resistive film 7 is preferably made of Pt, W, Mo, Ni, or $PbTiO_3$ doped with Nb or Sr which has a great positive temperature coefficient of resistance and which is stable at temperatures above 400° C. The sealing plate 3 may be made of resistive material to form a heater element. In this case, the resistive film 7 can be omitted. Specifically, the resistive sealing plate 3 is preferably made of ceramics such as molybdenum silicide, complex perovskite oxides, and lead titanate doped with Nb or Sr.

Figure 6:
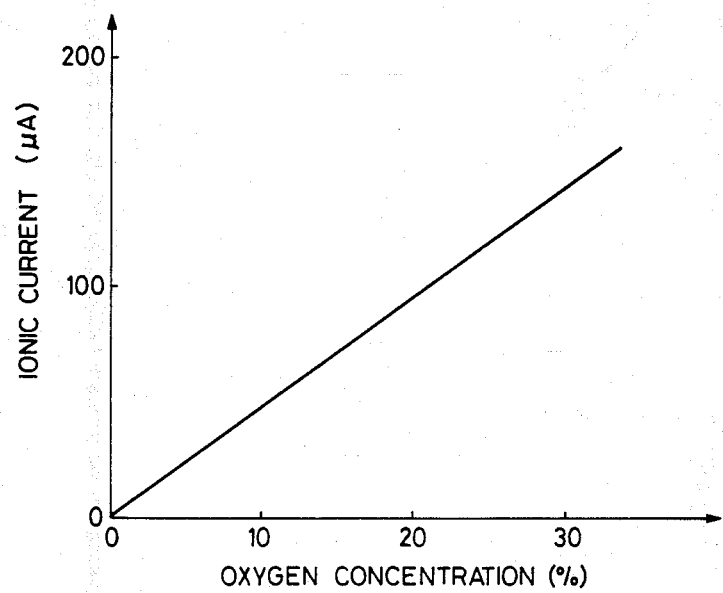
FIG. 6 is a graph showing the relationship between oxygen concentration and ionic current.

FIG. 6 shows an experimentally-obtained typical relationship between an environment oxygen concentration and a limited ionic current in an oxygen sensor of this invention. The oxygen sensor used in this experiment was designed as follows. The oxygen sensor included the electrolyte plate 1 of $ZrO_2$ doped with Y in 8 mol %, the spacing frame 2 of a fired glass film with a thickness of 50 micrometers, and the sealing plate 3 of a forsterite plate with a thickness of 0.5 millimeters and in the square form of 10 millimeters. The electrolyte plate 1 had a thickness of 0.2 millimeters and a square shape of 10 millimeters. Thick Pt film electrodes 41 and 42 with a diameter of 6 millimeters and a thickness of 5 micrometers had been preformed on the opposite surfaces of the electrolyte plate 1 by a firing process. The spacing frame 2 was formed in a spiral shape by a firing process. The window 5 was 400 micrometers in width, 25 millimeters in length, and 50 micrometers in height. A Pt resistive film 7 was formed on one surface of the sealing plate 3 by a firing process. The resistance of the resistive film 7 was about 22 ohms at room temperature. When an electric power of 2 W was applied to the resistive film 7, the oxygen sensor was heated up to about 400° C. and at that time the resistance increased to about 49 ohms. At a temperature of about 400° C., ionic currents were measured at various oxygen concentrations. The ionic current of 100 microamperes was obtained at the oxygen concentration of 21%. The ionic current increased linearly with the oxygen concentration in the range of 0-30%.

What is claimed is:

1. An oxygen sensor comprising:
   (a) an oxygen ion conductive solid electrolyte plate having first and second opposite surfaces;
   (b) first and second electrodes fixedly extending on the first and second surfaces of the electrolyte plate respectively;
   (c) an annular spacing frame hermetically secured to the first surface of the electrolyte plate and surrounding the first electrode, the spacing frame having an opening, wherein a height of the opening as measured with respect to the electrolyte plate is essentially equal to the thickness of the spacing frame; and
   (d) a sealing plate hermetically secured to the spacing frame and defining a chamber in conjunction with the electrolyte plate and the spacing frame, the chamber accommodating the first electrode and opening into an environment only via a window defined by the opening in the spacing frame, the window allowing oxygen molecules to flow from the environment into the chamber by diffusion.

2. The oxygen sensor of claim 1 wherein the window includes a spiral path with two open ends exposed to the environment and the chamber respectively.

3. The oxygen sensor of claim 1 wherein the spacing frame is composed of material selected from a group of a fired glass film and a Ti foil sandwiched between layers of an Ag-Cu alloy.

4. The oxygen sensor of claim 3 wherein the fired glass film comprises a mixture of a glass and small particles.

5. The oxygen sensor of claim 4 wherein the small particles comprise a material of $BaO-TiO_2-SiO_2$.

6. The oxygen sensor of claim 4 wherein the small particles have diameters of 10-50 micrometers.

7. The oxygen sensor of claim 4 wherein the fired glass film is composed of a cystalline glass comprising $PbO-ZnO-B_2O_3$.

8. The oxygen sensor of claim 7 wherein the sealing plate is made of material selected from a group of zirconia, glass, and forsterite.

9. The oxygen sensor of claim 3 wherein the Ag-Cu alloy comprises an Ag-Cu eutectic alloy.

10. The oxygen sensor of claim 1 wherein the electrolyte plate comprises zirconia stabilized with yttria, calcia, and baria.

11. The oxygen sensor of claim 1 wherein the spacing frame is entirely covered with the electrolyte plate and the sealing plate, and the window is placed inside edges of of the electrolyte plate and the sealing plate.

12. The oxygen sensor of claim 1 further comprising a resistive film fixedly extending on the sealing plate and forming a heater element.

13. The oxygen sensor of claim 12 wherein the resistive film is composed of material selected from a group of Pt, W, Mo, Ni, $PbTiO_3$ doped with Nb, and $PbTiO_3$ doped with Sr.

14. The oxygen sensor of claim 1 wherein the sealing plate forms a heater element.

15. The oxygen sensor of claim 14 wherein the sealing plate is composed of a ceramic selected from a group of molybdenum silicide, lead titanate doped with Nb, and lead titanate doped with Sr.

16. An oxygen sensor comprising:
   (a) an oxygen conductive solid electrolyte plate;
   (b) an electrode fixedly extending on the electrolyte plate;
   (c) a cover plate; and
   (d) an annular member extending between the electrolyte plate and the cover plate and hermetically bonded to the electrolyte plate and the cover plate, the annular member surrounding the electrode and defining a chamber in conjunction with the electrolyte plate and the cover plate, the chamber accommmodating the electrode, the annular member having an opening defining a window via which the chamber communicates with an environment, the window allowing oxygen molecules to flow from the environment into the chamber by diffusion, wherein the height of the opening measured with respect to the electrolyte plate is essentially equal to the thickness of the annular member.

17. The oxygen sensor of claim 16 wherein the window includes a spiral path with two open ends exposed to the environment and the chamber respectively.

18. The oxygen sensor of claim 16 wherein the electrolyte plate and the cover plate have portions projecting outward from the window and preventing dusts from moving to the window from the environment.

19. A method of manufacturing an oxygen sensor, comprising the steps of:
   (a) forming an electrode on a surface of an oxygen conductive solid electrolyte plate;
   (b) after the electrode is formed on the surface of the electrolyte plate, printing a predetermined pattern of glass paste on the surface of the electrolyte plate, wherein the predetermined pattern of the glass paste surrounds the electrode and wherein the glass paste comprises organic binder and glass particles;
   (c) placing a sealing plate on the printed pattern of the glass paste; and
   (d) firing an assembly of the electrolyte plate, the pattern of the glass paste, and the sealing plate, and thereby converting the pattern of the glass paste to a corresponding pattern of fired glass film and hermetically securing the electrolyte plate and the sealing plate to the pattern of the fired glass film, wherein the electrolyte plate, the sealing plate, and the pattern of the fired glass film define a chamber accommodating the electrode.

20. A method of manufacturing an oxygen sensor, comprising the steps of:
   (a) forming an electrode on a surface of an oxygen conductive solid electrolyte plate;
   (b) after the electrode is formed on the surface of the electrolyte plate, placing a predetermined pattern of Ti foil on the surface of the electrolyte plate, wherein the predetermined pattern of the Ti foil surrounds the electrode and wherein the Ti foil comprises outer layers made of an Ag-Cu alloy and an intermediate layer of Ti sandwiched between the outer layers;
   (c) placing a sealing plate on the pattern of the Ti foil; and
   (d) firing an assembly of the electrolyte plate, the pattern of the Ti foil, and the sealing plate, and thereby hermetically securing the electrolyte plate and the sealing plate to the pattern of the Ti foil, wherein the electrolyte plate, the sealing plate, and the pattern of the Ti foil define a chamber accommodating the electrode.

* * * * *